Figure 1:
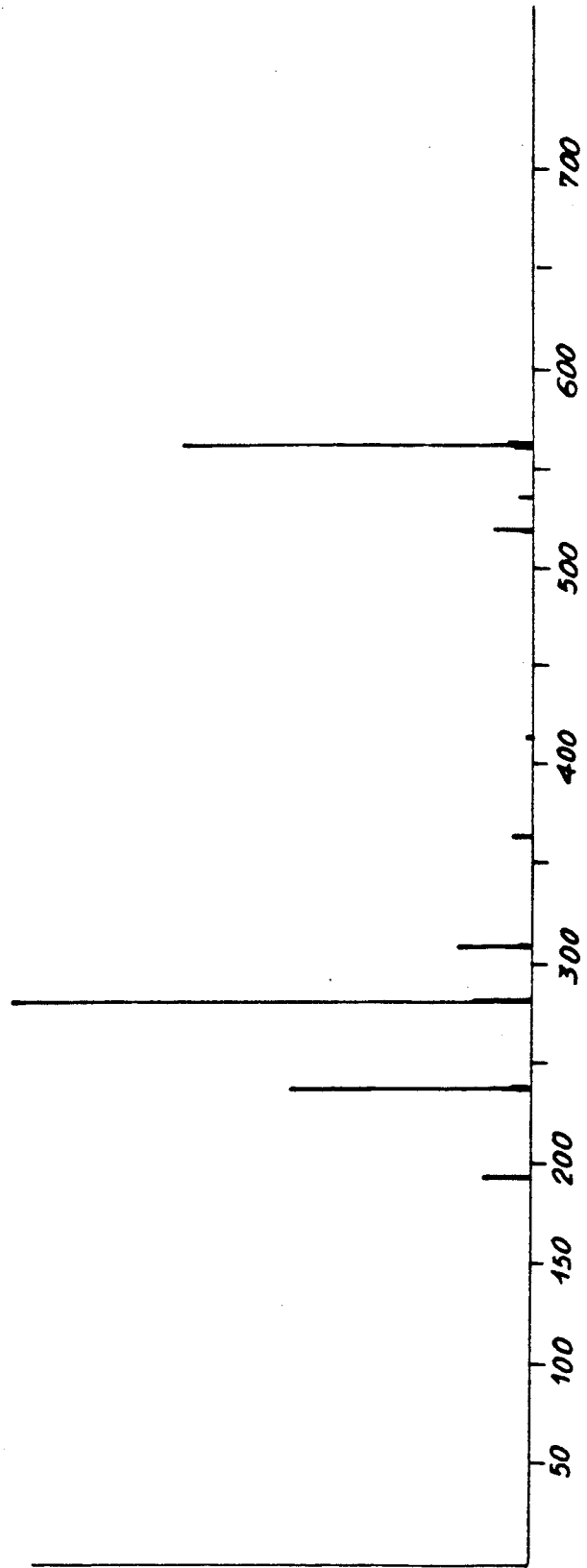

United States Patent [19]

Reveilleau et al.

[11] Patent Number: 5,151,517
[45] Date of Patent: Sep. 29, 1992

[54] DERIVATIVES OF TETRAHYDRO-2,3,6,7,1H,5H,11H-(1)BENZOPYRANO(6,7,8,I,J)QUINOLIZINONE-11 USABLE AS MARKERS FOR ORGANIC COMPOUNDS, PARTICULARLY BIOLOGICAL COMPOUNDS WITH A VIEW TO THEIR DETECTION BY CHEMILUMINESCENCE OR FLUORESCENCE

[75] Inventors: Pierre Reveilleau; Georges Mahuzier; Joseph Chalom, all of Paris; Robert Farinotti, Champigny s/Marne; Michel Tod, Margency; Edith Barre, Paris, all of France

[73] Assignee: Laboratories Eurobio, Les Ulis Cedex, France

[21] Appl. No.: 619,189

[22] Filed: Nov. 27, 1990

[30] Foreign Application Priority Data

Nov. 30, 1989 [FR] France ................. 89 15789

[51] Int. Cl.$^5$ ........................................ C07D 491/147
[52] U.S. Cl. ......................................................... 546/66
[58] Field of Search .......................................... 546/66

[56] References Cited

U.S. PATENT DOCUMENTS 4,736,032  4/1988  Fox et al. .......................... 546/66
5,082,942  1/1992  Mahuzier et al. .................. 546/66

FOREIGN PATENT DOCUMENTS 8912052  12/1989  PCT Int'l Appl.

OTHER PUBLICATIONS

Analytica Chimica Acta, 223 (1989) 309–317, "Chromatographic and Luminescence Properties of a 7-Aminocoumarin Derivative with Peroxyoxalate Chemiexcitation", M. Tod and M. Prevot.

*Primary Examiner*—Alan L. Rotman
*Assistant Examiner*—Catherine Scalzo
*Attorney, Agent, or Firm*—Pearne, Gordon, McCoy & Granger

[57] ABSTRACT

The invention relates to novel derivatives of tetrahydro-2,3,6,7,1H,5H,11H-(1)benzopyrano(6,7,8ij)-quinolizinone in accordance with the formula:

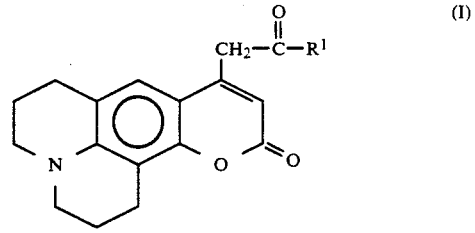

in which $R^1$ represents

1) $-NH-(CH_2)_n-R^2$ with n being an integer between 1 and 20 and $R^2$ representing $-N=C=S$ or $NH-CO-CH_2X$ with X representing I, Br or Cl, or 2) $-NH-(CH_2-CH_2-O)_m-CH_2-CH_2-R^3$ with m being an integer between 1 and 30 and $R^3$ representing a group chosen from among groups of formula $-NH_2$

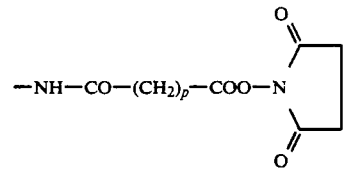

$-NH-CO-(CH_2)_p-CO-NH-NH_2,$ $-N=C=S,$ and $-NH-CO-CH_2X$ in which p is an integer from 1 to 10 and X represents Br, Cl or I. These derivatives can be use as markers for organic compounds, in particular biological substances, for the detection thereof by chemiluminescence or fluorescence.

10 Claims, 5 Drawing Sheets

DERIVATIVES OF TETRAHYDRO-2,3,6,7,1H,5H,11H-(1)BEN-ZOPYRANO(6,7,8,I,J)QUINOLIZINONE-11 USABLE AS MARKERS FOR ORGANIC COMPOUNDS, PARTICULARLY BIOLOGICAL COMPOUNDS WITH A VIEW TO THEIR DETECTION BY CHEMILUMINESCENCE OR FLUORESCENCE

The present invention relates to novel markers usable for marking organic and in particular biological compounds having —SH, —NH—, —NH$_2$ or —COO— groups, with a view to the detection of these compounds by chemiluminescence or fluorescence in determination processes of the liquid chromatography type, or in immunochemical methods.

It is known that the determination by liquid chromatography of amines, acids and their corresponding anhydrides, having no spectral properties requires, in order to obtain a high sensitivity, the transformation of these compounds by means of marking reagents in order to give them absorption, fluorescence or chemiluminescence properties.

The use of markers of this type for the detection of carboxylic derivatives or amines is in particular described by H. Cisse, R. Farinotti, S. Kirkiacharian and A. Dauphin in Journal of Chromatography, 225, 1981, pp. 509-515; by M. Tsitini Tsamis, A. M. Mange, R. Farinotti and G. Mahuzier in Journal of Chromatography, 277, 1983, pp. 61-69; by N. Kubab, R. Farinotti and G. Mahuzier in Analusis, 1986, v. 14, no. 3, pp. 125-130; and by D. Amir and E. Haas in Int. J. Peptide Protein Res., 26, 1986, pp. 7-17.

In liquid chromatography determination processes, in particular chemiluminescent markers are sought, because analysis by chemiluminescence is subject to a large amount of development making it possible to improve the sensitivity of the determination. Thus, chemiluminescence methods make it possible to achieve a detection limit of approximately 1 femtomole, whereas in spectrofluorimetric methods the detection limit currently reached is a few hundred femtomoles.

A detection method by chemiluminescence in liquid chromatography is in particular described by M. Tod, R. Farinotti and G. Mahuzier in Analusis, 1986, v. 14, no. 6, pp 271-280.

The presently used chemiluminescent markers such as orthophthalaldehyde, fluorescamine and anthracene and dansylated derivatives suffer from certain disadvantages. Thus, orthophthalaldehyde and fluorescamine are not very sensitive. Anthracene derivatives are inhibited by dissolved oxygen and dansylated derivatives are inhibited by certain excitation reaction products. Moreover, certain chemiluminescent markers have a by no means negligible toxicity, which is in particular the case with anthracene and dansylated derivatives.

As a result of recent research it has been found that coumarin nuclei are of certain interest, because they have an equivalent sensitivity to the highest performance products, which have neither toxicity nor sensitivity with respect to the conventional inhibitors, such as dissolved oxygen, halides and nitro derivatives. In addition, they are easy to use under varied excitation and chromatography conditions.

Thus, M. Tod et al described in Anal. Chem. Acta, 223, 1989, pp, 309-317 a novel 7-amino coumarin derivative, namely luminarine-1, which can be used as a marker for primary and secondary amines and which complies with the formula:

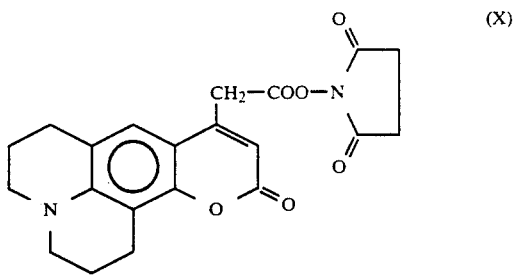

Although the properties of luminarine-1 are very interesting, research has been continued in order to find other derivatives which, on the one hand have a better hydrosolubility than luminarine-1 and on the other hand are more suitable for marking biological molecules, such as antibodies and oligonucleotide probes and other affinity ligands.

The present invention specifically relates to novel coumarin derivatives, which are derivatives of tetrahydro-2,3,6,7,1H,5H,11H-(1)benzopyrano(6,7,8,ij)-quinolizinone-11 have improved properties.

According to the invention, the derivatives of tetrahydro-2,3,6,7,1H,5H,11H-(1)benzopyrano(6,7,8,ij)-quinolizinone-11 comply with the formula:

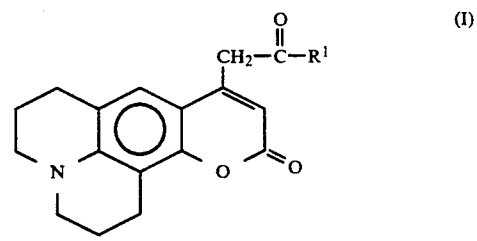

in which $R^1$ represents:
1) NH—(CH$_2$)$_n$—R$^2$ with n being an integer from 1 to 20 and $R^2$ representing —N=C=S or NH—CO—CH$_2$X with X representing I, Br or Cl, or
2) NH—(CH$_2$—CH$_2$—O)m—CH$_2$—CH$_2$—R$^3$ with m being an integer from 1 to 30 and $R^3$ representing a group chosen from among groups of formula

—NH$_2$

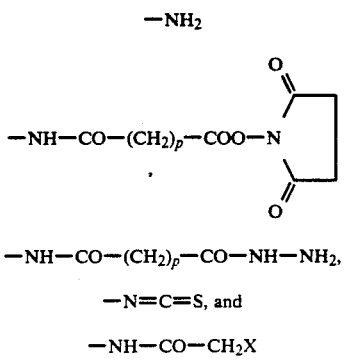

—NH—CO—(CH$_2$)$_p$—CO—NH—NH$_2$,

—N=C=S, and

—NH—CO—CH$_2$X in which p is an integer between 1 and 10 and X represents Br, Cl or I.

In these novel derivatives, the use of the coumarin nucleus of formula:

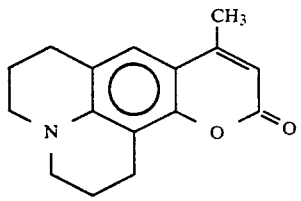

makes it possible to obtain improved fluorescence and chemiluminescence properties. Moreover, the choice of an appropriate —CO—R¹ group fixed to the coumarin nucleus makes it possible to obtain markers usable for a large number of organic compounds and in particular biological substances.

Thus, the novel derivatives of the invention have the advantage of a good stability, of being usable as markers for different compounds, of being usable in the normal or reverse phase, of not being inhibited by the conventional quenchers such as dissolved oxygen, halides and nitrates, of not having toxicity and of rapidly reacting with the compounds to be marked under relatively gentle conditions.

According to a first embodiment of the invention, the derivatives of tetrahydro-2,3,6,7,1H,5H,11H(1)benzopyrano(6,7,8,ij)quinolizinone-11 comply with the formula:

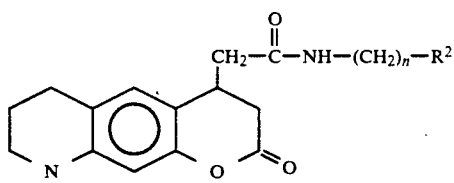

in which n is an integer between 1 and 20 and $R^2$ is $N=C=S$ or $NH-COCH_2X$ with X representing I, Br or Cl. Preferably, in this first embodiment n is an integer between 1 and 12.

Examples of derivatives complying with this first embodiment are those for which n is equal to 4 and $R^2$ represents $NHCOCH_2I$ or $N=C=S$.

The derivatives according to this first embodiment of the invention having a halogenoacetomido terminal group $NH-CO-CH_2X$, e.g. an iodoacetamido group are very interesting, because they are able to mark sulphydryl (or thiol) groups, either in small molecules such as medicaments such as Captopril, cysteine and cysteamine, or in proteins having the same group.

Thus, they are able to react with compounds having said thiol group. The derivative formed by this reaction can be separated e.g. by liquid chromatography and can be detected by absorptiometry, fluorimetry or chemiluminescence.

In this first embodiment, the derivatives in which $R^2$ is $-N=C=S$ are also of great interest. Thus, these molecules can react with primary amines and can in particular be used for marking proteins and especially antibodies.

For example, on reacting one of these derivatives with pentylamine, the corresponding derivative is obtained in particularly gentle conditions.

According to a second embodiment of the invention, the derivatives of tetrahydro-2,3,6,7,1H,5H,11H-(1)benzopyrano(6,7,8,ij)quinolizinone-11 comply with the formula:

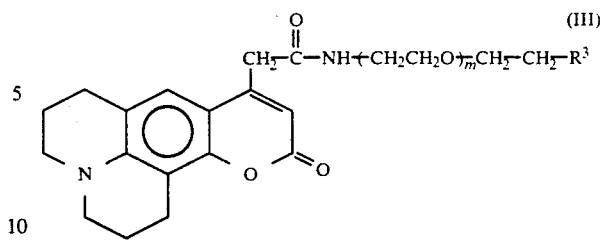

in which m is an integer between 1 and 30 and $R^3$ is as defined hereinbefore. Preferably, m is an integer from 1 to 6. Examples of such derivatives are those for which m is 5.

The derivatives complying with this second embodiment have in their sidechain a poly(oxy-1,2-ethanediyl) part related to polyethylene glycol. This part gives a hydrosolubility to the derivatives, which also remain soluble in most organic solvents.

This hydrosolubility property has major advantages in the marking of biological molecules (proteins or DNA). It eliminates the presence, in the immediate vicinity of the biological molecule, of a hydrophobic group such as the main quinolizinone nucleus, or a sidechain with 4 carbons as in the case of the derivatives corresponding to the first embodiment of the invention. This advantage is further reinforced by the length of the poly-(oxo-1,2-ethanediyl) part, which can always be adapted to the precise need.

In addition, these derivatives can have even more suitable applications than those referred to hereinbefore, particularly in immunology (marking of antibodies) or in molecular biology (DNA probes).

Moreover, the presence of the oxo-1,2-ethanediyl arm favours the formation of hydrogen bonds. This effect is beneficial particularly with the antigen-antibody bonds, or in molecular hybridization (nucleic probes). In this second embodiment, the reactivity of each derivative is determined by the nature of the $R^3$ group.

Thus, when $R^3$ represents $NH_2$, the derivatives can react with the compounds and biological substances having a carboxylic function (in the presence of a coupling agent), their anhydrides and their esters, in particular with all the acids in activated form, such as hydroxysuccinimide esters, e.g. with those of greatest interest in immunology such as NHS biotin of formula:

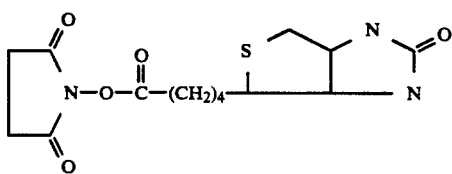

or NHS-LC-biotin.

This is very interesting, because biotin is very widely used in biology, immunology, etc., where advantage is taken of its very considerable affinity ($10^{15}M^{-1}$) for avidin, which is a glycoprotein extracted from egg white having a mass of 66000 and formed by four identical subunits, each of which can be fixed to a biotin molecule.

Thus, it is possible to use the derivative of formula III with $R^3$ representing $NH_2$ for detecting a compound having a —COO— group. In this case, the derivative of formula III is reacted with the compound to be detected, in order to form a derivative of the compound to be detected which is detected by absorptiometry, fluorimetry or chemiluminescence, using liquid chromatography or biochemical methods, which may or may not use specific ligands.

When $R^3$ represents

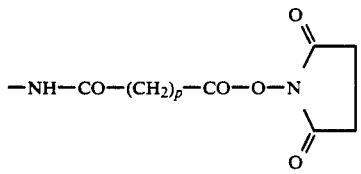

in which p is an integer from 1 to 10, preferably 1 to 3, e.g. 2, the derivatives can react with primary and secondary amines in an aqueous or non-aqueous medium. This is particularly interesting for the marking of amine functions of biological substances such as antibodies, or modified DNA probes having a primary amine function.

When $R^3$ represents —NH—CO—$(CH_2)_p$—CO—NH—$NH_2$ the derivatives can react with aldehydes (and in particular with aldehyde groups obtained by the periodic oxidation of glycoproteins). They can also react on DNA chains by the transamination of cytosine groups.

When $R^3$ represents N=C=S or —NH—CO—$CH_2$X, the derivatives have the same reactivity as the derivatives of the first embodiment for which $R^2$ is —N=C=S or —NH—CO—$CH_2$X.

The derivative formed after reacting with the primary or secondary amine can be detected by absorptiometry, fluorimetry or chemiluminescence using liquid chromatography or biochemical methods, which may or may not use specific ligands.

In the latter case which corresponds to the maximum sensitivity, the excitation reaction can use an oxalic ester and hydrogen peroxide which form peroxyoxylate, which is a high energy reaction intermediate, which transfers its energy to the derivative formed, which is deexcited whilst emitting light. This determination by chemiluminescence can be applied to molecules of biochemical or pharmacological interest with a view to metabolic or pharmacokinetic studies, particularly the determination of amino acids, biogenous amines of the histamine type, neuromediators of the catecholamine type, hormonal polypeptides and metabolites of phenothiazines, imipraminics, etc.

In the case of uses in biology, the derivatives can react with aminobiological substances, e.g. antibodies, an oligonucleotide modified by an amino group, or some other affinity ligand carrying an amino group. The thus formed marked products can react in the homogeneous (liquid phase) or in the solid-liquid phase on an appropriate support/complementary ligand.

The novel coumarin derivatives according to the invention can be prepared by conventional processes. Thus, it is possible to prepare the derivatives of formula (II) for which $R^2$ represents NHCOCH$_2$X by a process consisting of reacting a derivative of tetrahydro-2,3,6,7,1H,5H,11H-(1)benzopyrano(6,7,8,ij)quinolizinone-11 compound of formula

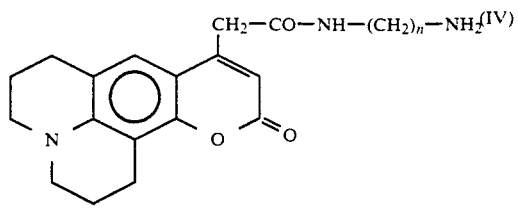

with a halogenoacetic anhydryde, in the presence of a trialkyl amine such as triethyl amine.

This corresponds to the following reaction:

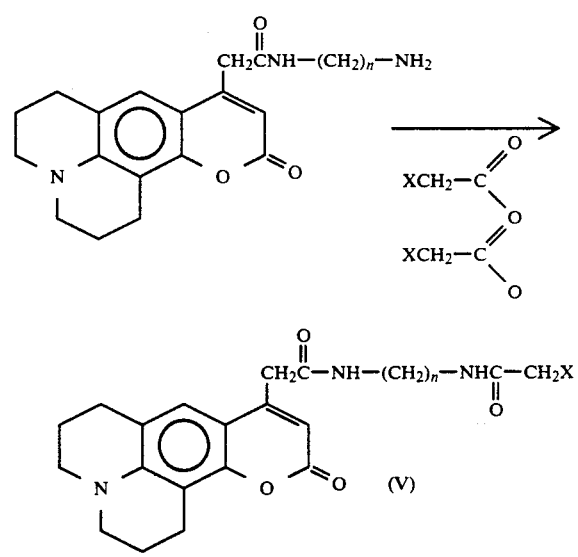

The derivative of formula (IV) can be prepared by a process comprising the following successive stages:

1) reacting the 8-hydroxyjulolidine of formula:

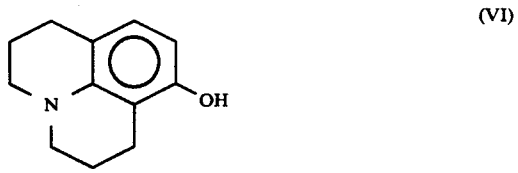

with an oxo-3-glutaric acid alkyl ester of formula:

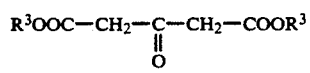

in which $R^3$ is an alkyl radical, to form a compound of formula:

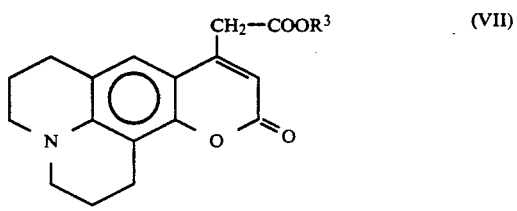

2) hydrolyze the alkyl ester of formula (VII) obtained previously to obtain the acid of formula:

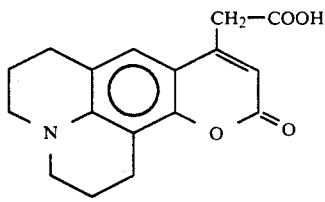 (VIII)

3) reacting the acid of formula (VIII) with the dihydroxysuccinimide oxalate of formula:

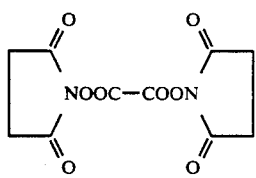 (IX)

or hydrosuccinimide in the presence of a coupling agent for forming the derivative of formula:

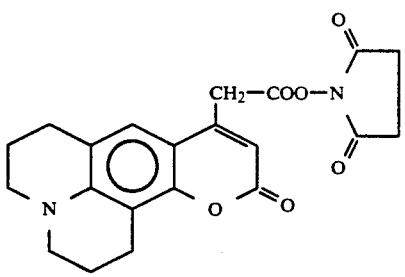 (X)

4) reacting the derivative of formula (X) with a diaminoalkane of formula:

H₂N—(CH₂)$_n$—NH₂        (XI)

in which n has the meaning given hereinbefore.

In the latter process, the first stage can be carried out by refluxing, accompanied by stirring, the 8-hydroxyjulolidine with the oxo-3-glutaric acid alkyl ester, in the presence of anhydrous zinc chloride and in alcoholic solution. The compound of formula (VII) obtained can be separated by extraction by means of an organic solvent such as ethyl acetate.

The oxo-3-glutaric acid alkyl ester is preferably the methyl or ethyl ester.

In the second stage of the process, it is possible to carry out the hydrolysis of the alkyl ester of formula (VII) by an aqueous soda solution in an alcoholic solution e.g. constituted by methanol.

The third stage of the process can e.g. be performed by reacting the acid of formula (VIII) with the dihydroxysuccinimide oxalate in an anhydrous organic solvent, in the presence of anhydrous triethyl amine. Under these conditions, it is possible to obtain the coumarin derivative of formula (X) with a high degree of purity of approximately 90%.

The coumarin derivatives according to formula XII)

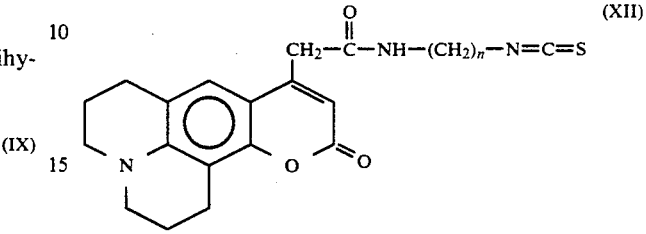 (XII)

can be prepared by the action of thiocarbonyl diimidazole on the aforementioned derivative of formula (IV). The following reaction diagram is used:

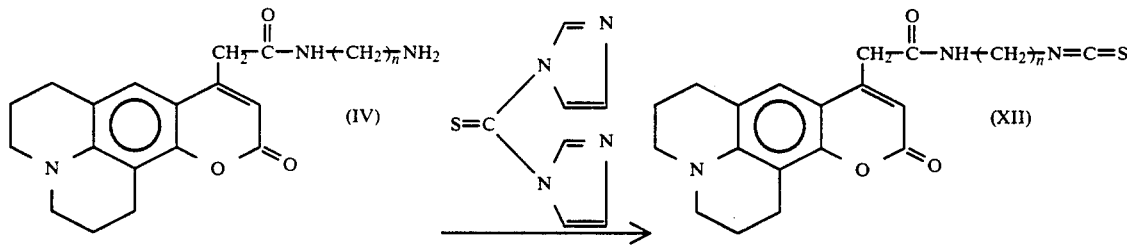

The coumarin derivatives according to formula:

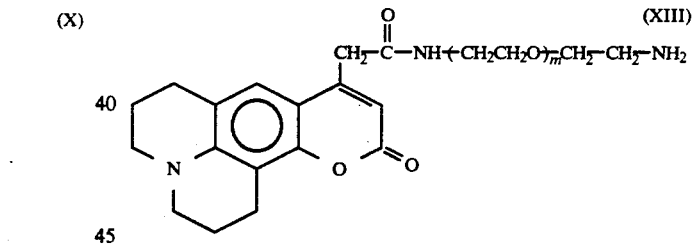 (XIII)

in which m is an integer from 1 to 30, can be prepared by a process consisting of reacting the compound of formula:

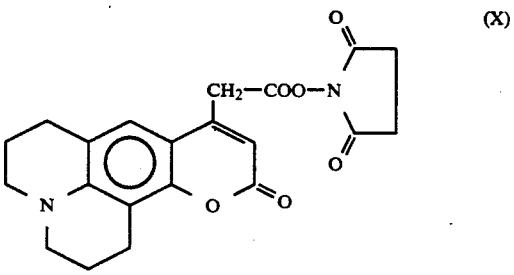 (X)

with an excess of poly-(oxy-1,2-ethanediyl)-diamine of formula:

H₂N—(CH₂CH₂O)$_m$—CH₂—CH₂NH₂        (XIV)

in which m has the meaning given hereinbefore.

The coumarin derivatives according to formula:

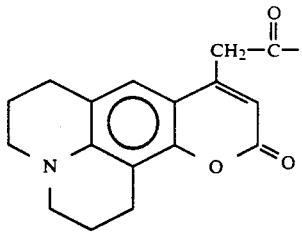 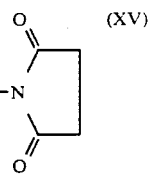 (XV)

in which m is an integer from 1 to 30 and p is an integer from 1 to 10, can be prepared by a process comprising the following successive stages:

1) reacting a compound of formula:

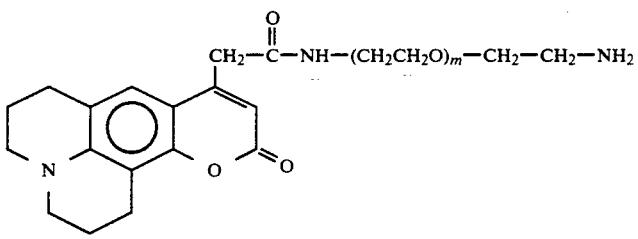

in which m has the meaning given hereinbefore, with a diacid anhydride of formula:

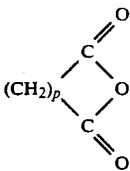 (XVI)

to obtain an acid of formula:

2) reacting the acid of formula (XVII) with hydroxysuccinimide in the presence of a coupling agent to form the derivative of formula (XV).

The coupling agent can e.g. be dicyclohexyl carbodiimide.

The derivatives of formula (XV), particularly those for which p=1, can also be prepared by the reaction of thederivative of formula (XIII) with the benzyl monoester of dicarboxylic acid of formula:

HOOC—(CH$_2$)$_p$—COOCH$_2$C$_6$H$_5$ followed by debenzylation by hydrogenation in order to obtain the acid of formula (XVII) which is then reacted as hereinbefore with the hydroxysuccinimide.

Acid (XVII) is prepared in accordance with the following diagram:

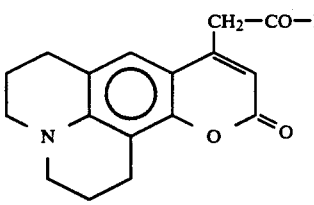 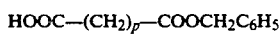 (XVII)

(XIII) + HOOC—(CH$_2$)$_p$—COOCH$_2$C$_6$H$_5$ 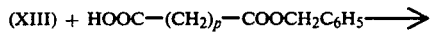

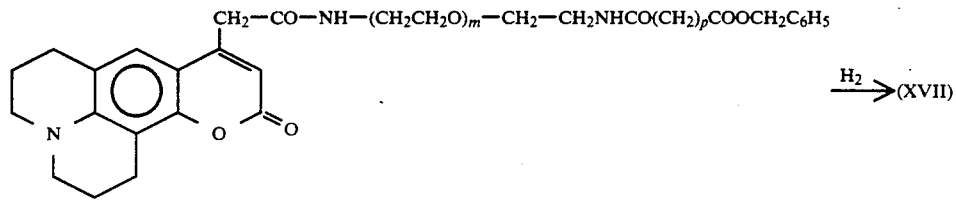

$\xrightarrow{H_2}$ (XVII)

The coumarin derivatives according to formula:

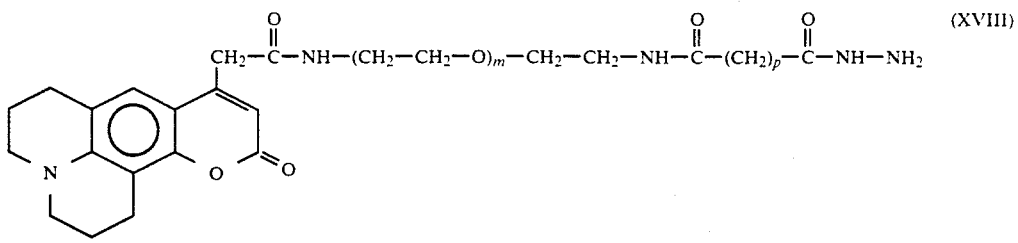

can e.g. be prepared by the action of a hydrazine hydrate excess, e.g. in DMF/water phase, on compounds of formula (XV) in accordance with the following diagram:

The coumarin derivatives according to formula:

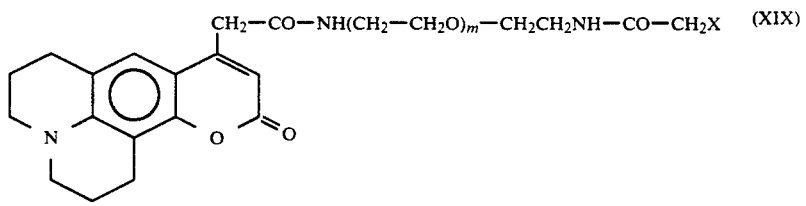

can be prepared from derivatives of formula (XIII) by reacting them with a halogeno acetic anhydride in the presence of a trialkyl amine such as triethyl amine. This

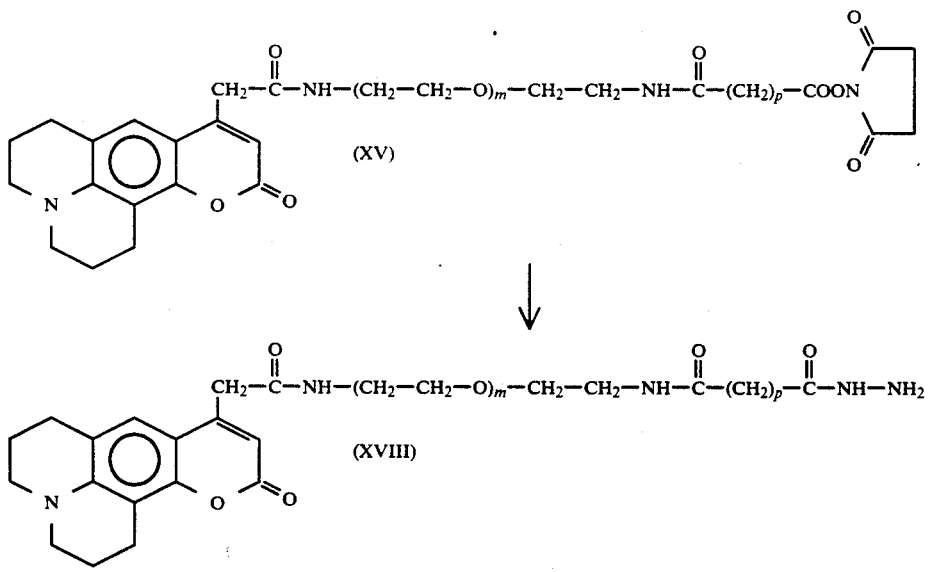

corresponds to the following reaction diagram:

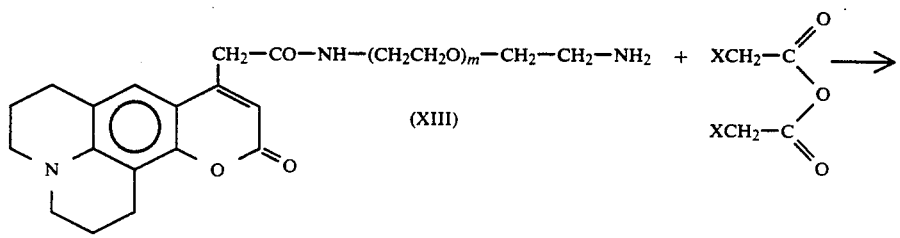

-continued

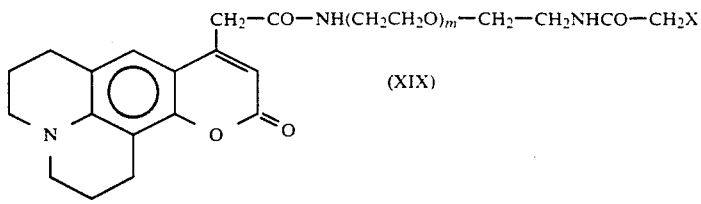

(XIX)

The coumarin derivatives according to formula:

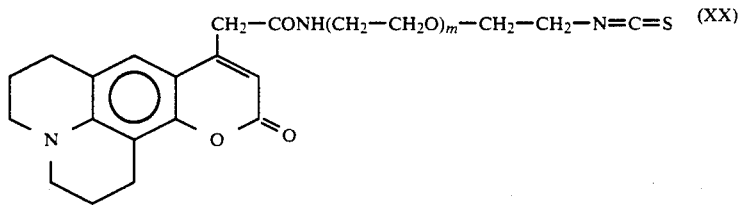

can be prepared from derivatives of formula (XIII) by reacting with thiocarbonyl diimidazole according to the following reaction diagram:

Tsamis et al in Journal of Chromatography, 277, 1983, 61-69; by D. Amir and E. Haas in Int. J. Peptide Protein Res., 26, 1986, pp.7-17; by H. Cisse et al in Journal of Chromatography, 225, 1981, pp.509-515; and by M.

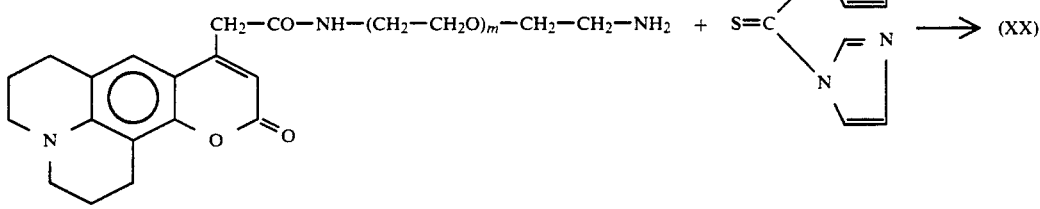

The starting products used in these different preparation methods for the coumarin derivatives according to the invention are commercially available or can be prepared by conventional processes from commercially available products.

As stated hereinbefore, the coumarin derivatives according to the invention can react with different organic compounds, e.g. amines, thiols, carboxylic acids, their anhydrides or their esters.

Moreover, these coumarin derivatives can be used as markers for organic compounds having primary or secondary amine, thiol or carboxylic acid functions and can be used in the detection of these compounds in determination methods, e.g. liquid chromatography, or in immunochemical methods which may or may not use specific ligands. Detection can be carried out by absorptiometry, fluorimetry or chemiluminescence using conventional methods of the type described by M. Tsitini Tod et al in Analusis, 1986, v.14, no.6, pp.271-280.

Thus, the invention also relates to a process for the detection of a compound having a primary or secondary amine function consisting of reacting the compound to be detected with a derivative complying with the formula:

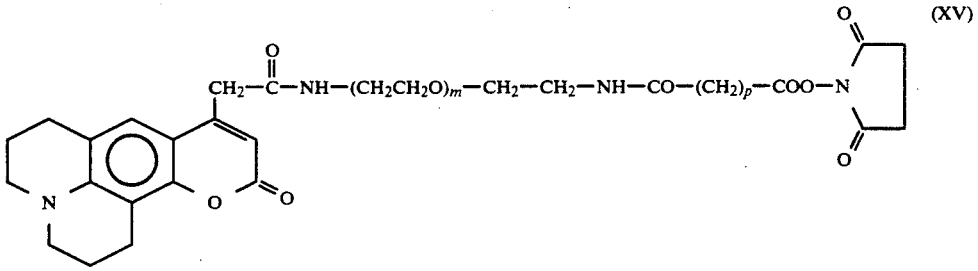

in which m is an integer from 1 to 30 and p is an integer from 1 to 10, in order to form a derivative of the compound to be detected, followed by separating said derivative and then detecting said derivative by absorptiometry, fluorimetry or chemiluminescence.

In this process for the detection of compounds having an amine function, it is also possible to use derivatives of formula (XII) or (XX).

Using the same process it is possible to detect a compound having a SH group or a —COO— group, respectively using the derivatives of formula (V) or (XIX) or formula (XIII).

In all cases, preference is given to carrying out the detection by chemiluminescence using an oxalic ester and hydrogen peroxide. For example, the oxalic ester can be bis-(trichloro-2,4,6-phenyl)-oxalate (TCPO) or bis-(dinitro-2,4-phenyl)-oxalate (DNPO).

Figure 2:
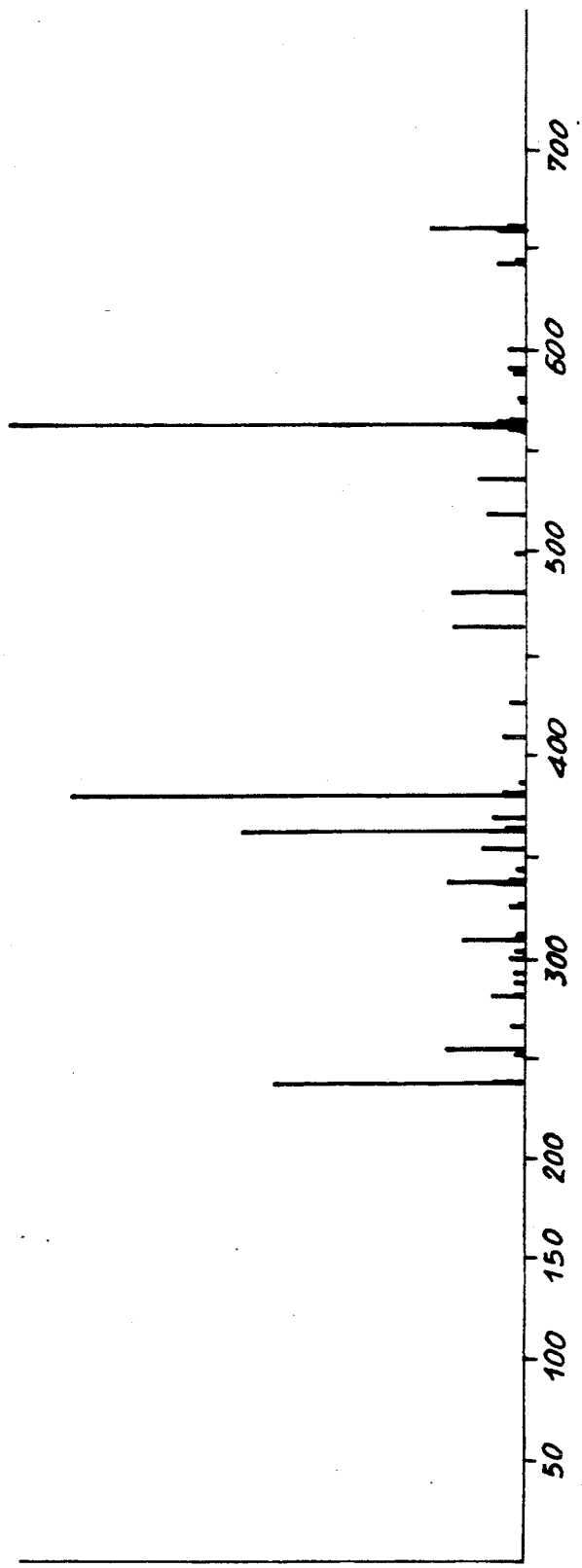
Figure 3:
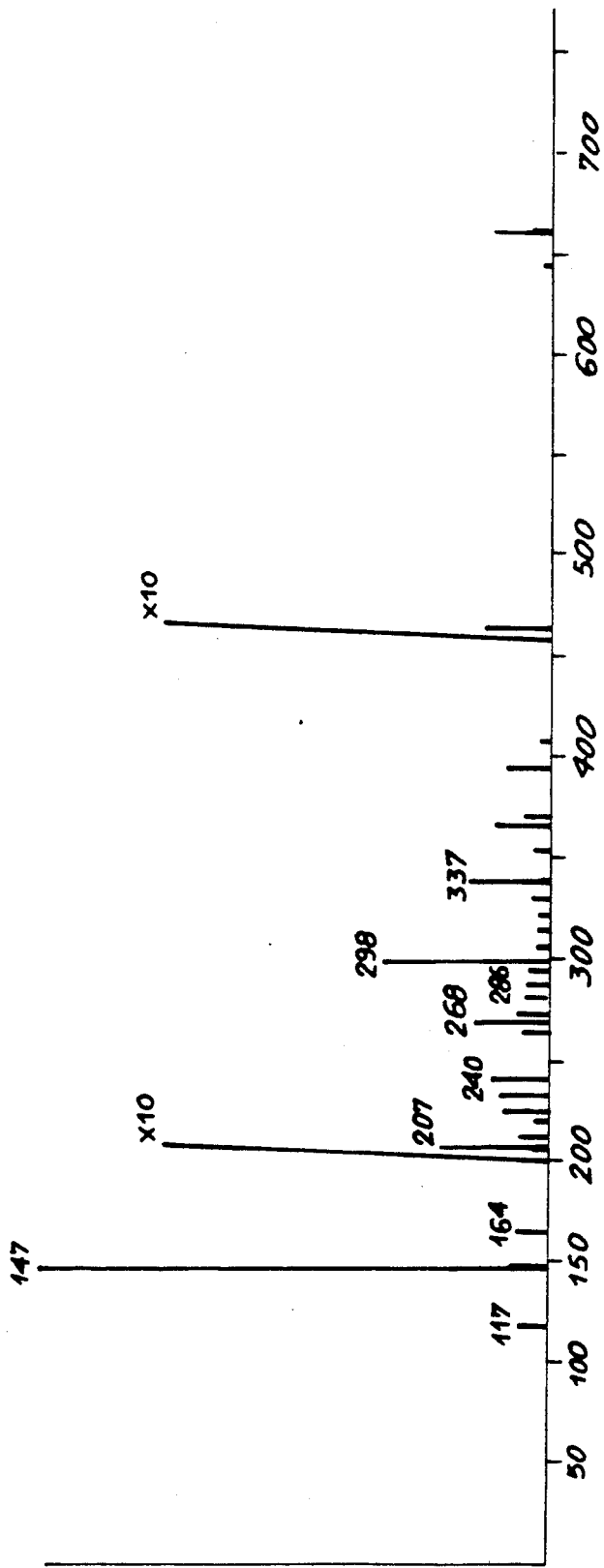
Figure 4:
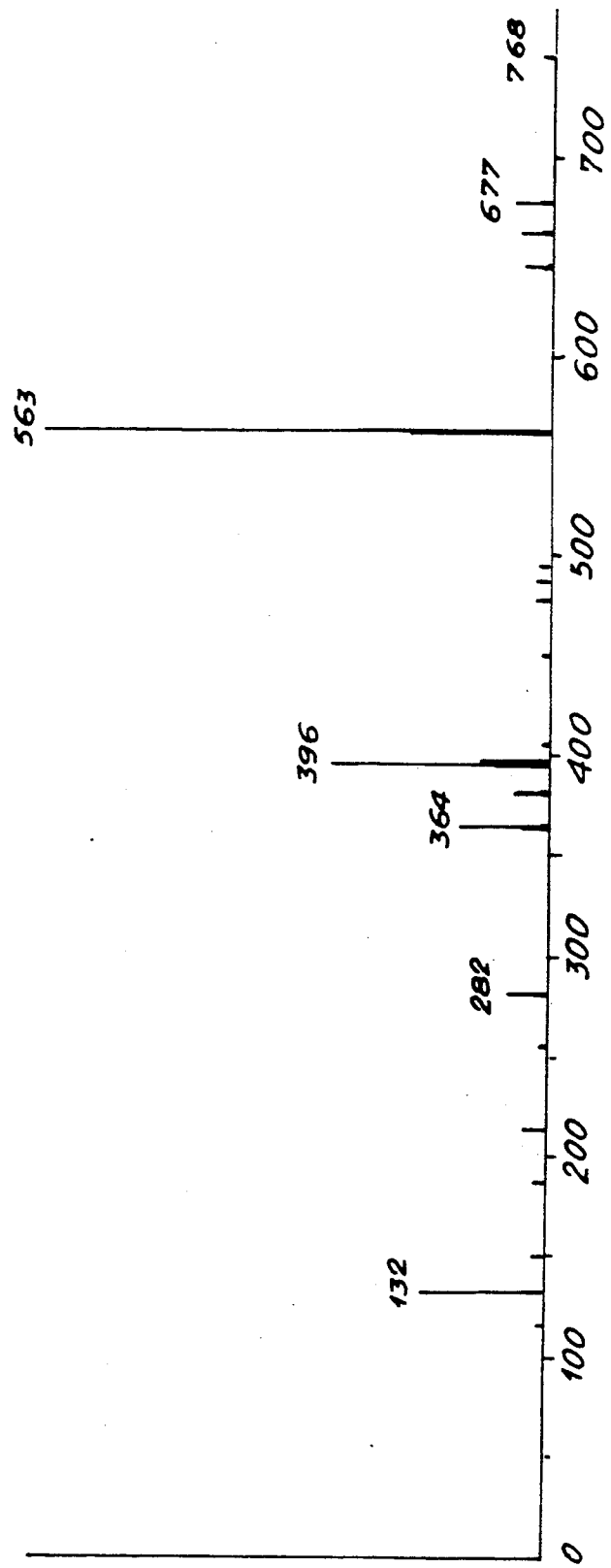
Figure 5:
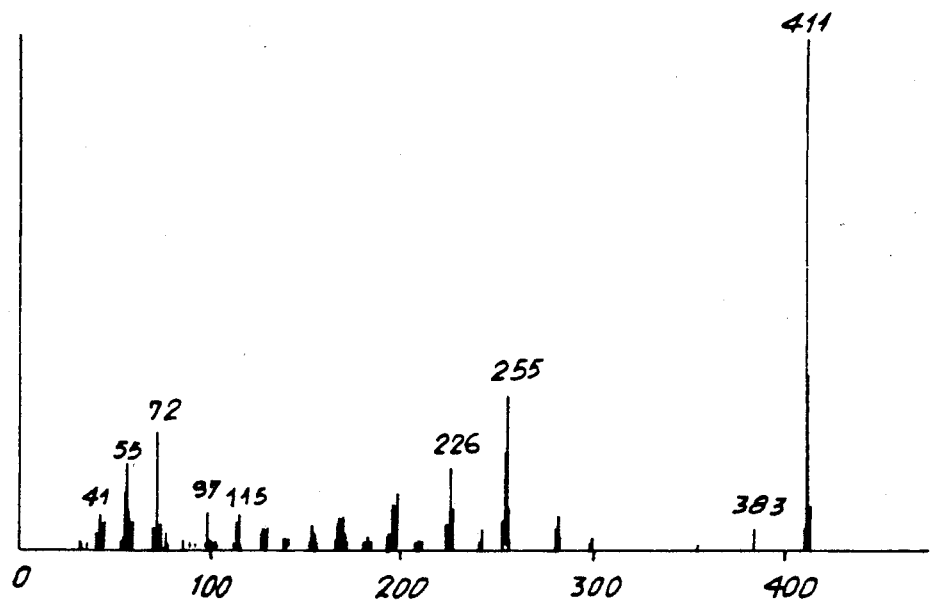
Figure 6:
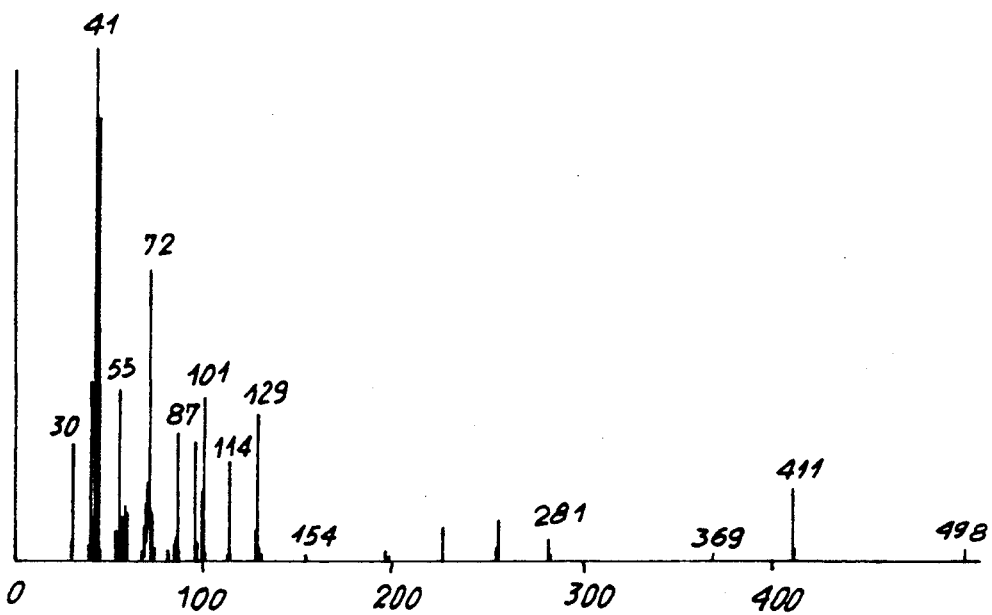

The invention will be better understood from studying the following illustrative and non-limitative examples with reference to the attached drawings, wherein show:

FIG. 1 The mass spectrum of luminarine-6.
FIG. 2 The mass spectrum of the derivative obtained by reacting succinic anhydride with luminarine-6.
FIG. 3 The mass spectrum of luminarine-7.
FIG. 4 The mass spectrum of luminarine-8.
FIG. 5 The mass spectrum of luminarine-9.
FIG. 6 The mass spectrum of luminarine-9 after reacting with pentyl amine.

EXAMPLE 1

Synthesis of luminarine-5 according to formula

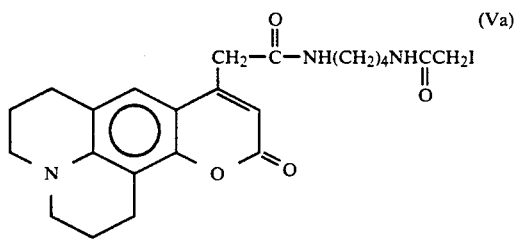
(Va)

This derivative complies with formula (V) with $N=4$ and $X=I$.

1) Preparation of the derivative of formula (IV) with $n=4$ ((IVa)

a) Preparation of the compound of formula (VII) with $R^3$ representing the ethyl radical (VIIa)

The reaction performed here corresponds to the following reaction diagram:

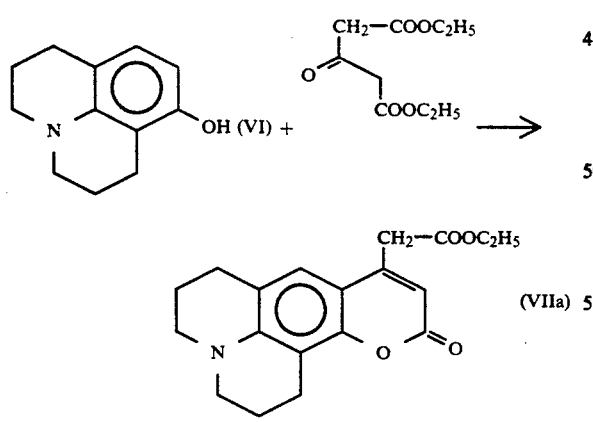

Into a container are introduced 2.12 g of 8-hydroxyjulolidine, 2.22 g of oxo-3-glutaric acid ethyl ester, 1.71 g of anhydrous zinc chloride and 6 ml of anhydrous ethanol, followed by refluxing for 24 h, accompanied by stirring and protected from moisture. After cooling, the solution is introduced into 200 ml of water, followed by extraction by 200 ml and then 100 ml of ethyl acetate. The organic phase is washed with water, dried on magnesium sulphate and concentrated to dryness. This is followed by recrystallization in 5 parts of ethyl acetate, which gives the ethyl ester of formula (VII) with a 56% yield.

b) Hydrolysis of the ethyl ester of formula (VIIa) obtained previously

Into a container are introduced 2 g of the previously obtained ethyl ester with 42 ml of an aqueous 1.2% wt/vol solution and 40 ml of methanol, followed by heating to 45° C. for 1 hour. After cooling, the reaction medium is extracted by 50 ml and then 40 ml of chloroform. After degassing, the aqueous phase is acidified with 16 ml of 3N hydrochloric acid and stirring of the reaction mixture is maintained for 15 min. The pH is adjusted to 6.5 with 13 ml of 2.5N soda. The precipitate formed is filtered, rinsed with water and dried. This gives the acid of formula (VIII) with a 90% yield.

c) Obtaining the derivative of formula (X), luminarine-1

In said third stage, the acid of formula (VIII) obtained in the preceding stage is reacted with dihydroxysuccinimide oxalate according to the following reaction diagram:

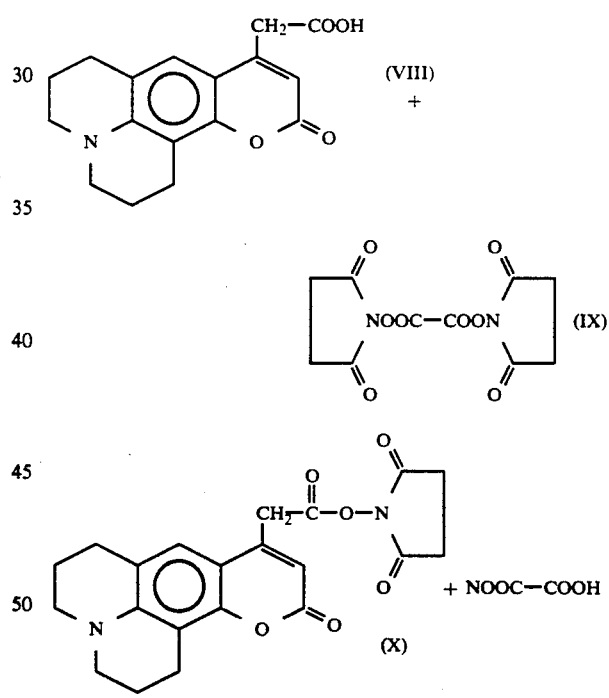

Into a container are introduced 11.26 g (0.0377 mole) of the acid of formula (VIII), 10.62 g (0.0415 mole) of dihydroxysuccinimide carbonate, 3.81 g (0.0377 mole) of anhydrous triethyl amine and 560 ml of anhydrous acetonitrile. The mixture is stirred, protected from moisture for 1 hour at ambient temperature and then for 1 hour at 35° to 40° C. This is followed by filtration of a slight insoluble, vacuum concentration and purification by silica gel chromatography using as the elution solvent the dichloromethane/tetrahydrofuran (THF) mixture with a volume ratio of 1:1. Fractions 11 to 14 are concentrated, which gives the derivative of formula (X), luminarine-1, with a 21% yield.

d) Obtaining the derivative of formula (IVa) with n=4

The starting product is the purified derivative of formula (X), luminarine-1, which is reacted with 1,4-diaminobutane according to the following reaction diagram:

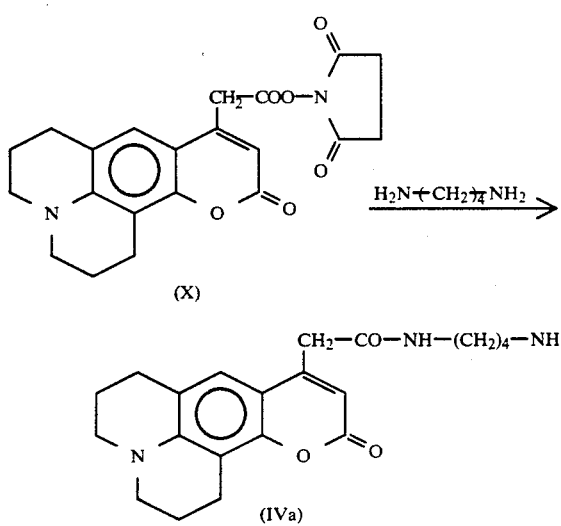

In a one liter round-bottomoed flask are reacted 16.5 g of luminarine-1 (X) (41.6 mmoles) and 18.3 g of 1,4-diaminobutane (107 mmoles) in 400 ml of anhydrous THF, accompanied by stirring and for 24 hours. A maroon coloured insoluble is filtered.

The mother liquors are concentrated to dryness, the residue taken up in 100 ml of dichloromethane and extraction takes place by 5×100 ml of water to eliminate the excess 1,4-diaminobutane. The solvent is concentrated to dryness. The residue is stirred in 25 ml of dichloromethane giving a 10.6 g (69% yield).

The structure of the compound obtained is checked by mass spectrometry and NMR.

2. Preparation of luminarine-5, the derivative of formula (Va)

The starting substance is derivative (IVa), which is reacted with iodoacetic anhydride in the presence of triethyl amine according to the following diagram:

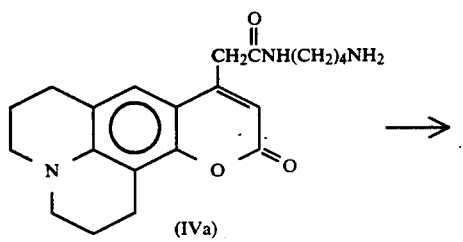

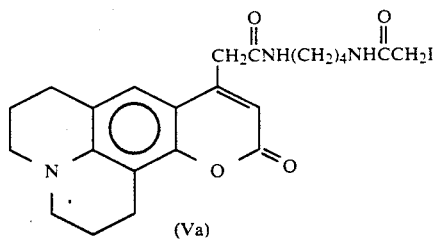

158 mg of the derivative (IVa) (0.4 mmole), 212.4 mg of iodoacetic anhydride and 84 µl (0.6 mmole) of triethyl amine are dissolved in 1 ml of dimethyl formamide. Reaction takes place for 2 hours at ambient temperature and protected from light. Precipitation takes place by the addition of 4 ml of distilled water, followed by vacuum filtering. Drying takes place on phosphoric anhydride. This gives luminarine-5 with a 76% yield.
Elementary analysis: I calculated=23.6%;
I found=22.96%.
TLC (thin layer chromatography),
Fluorescent silica,
System BuOH/AcOH/H2O 70/20/10,
1 fluorescent spot (Rf=0.75).

EXAMPLE 2

Use of lumarine-5 for marking the thiol function of cysteamine 5.3 mg of luminarine-5 (1·10−2 mmole) and 7.7 mg of cysteamikne (0.1 mmole) are reacted in a borate buffer at pH8 (1 ml). After reacting for 1 hour TLC reveals the complete disappearance of luminarine-5 and the formation of the fluorescent derivative (Rf=0.4) of the thiol which has reacted in accordance with the reaction:

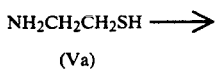

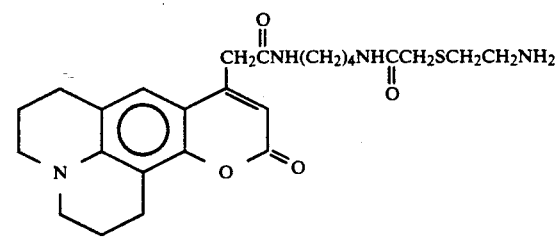

EXAMPLE 3

Synthesis of luminarine-6 of formula

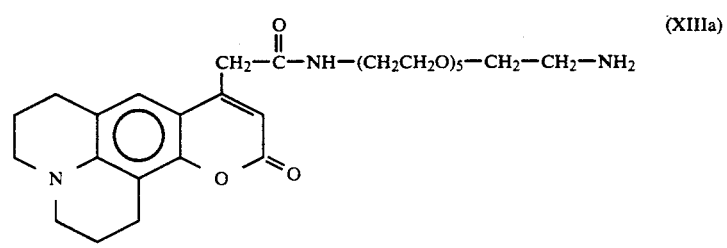

This derivative is in accordance with formula (XIII) with m=5

The luminarine-1, derivative (X), obtained in stage c) of example 1 is reacted with 1,17-diamino-3,6,9,12,15-pentaoxaheptadecane (XIIa), in dichloromethane:

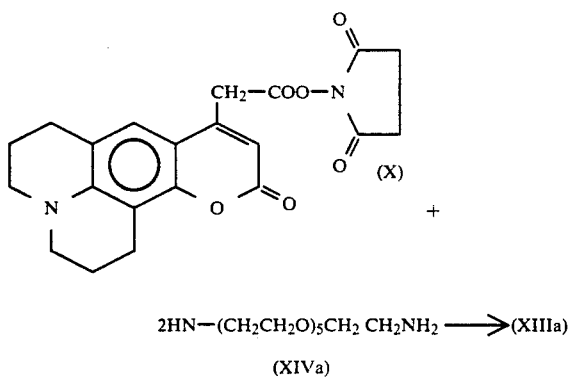

2HN—(CH₂CH₂O)₅CH₂ CH₂NH₂ ⟶ (XIIIa)

(XIVa)

In a sealed tube protected from light stirring takes place for 24 hours at ambient temperature of 139 mg (0.35 mmole) of luminarine-1 (X) and 392 mg (1.4 mmole) of 1.17 diamino-3,6,9,12,15-pentaoxaheptadecane (XIVa) in 2 ml of dichloromethane.

The dichloromethane is evaporated and taken up by 10 ml of water, which eliminates a non-hydrosoluble impurity. Extraction takes place by 10 ml of dichloromethane and product (XIIIa) passes into the dichloromethane and the amine excess remains in the aqueous phase.

This is followed by drying and evaporation of the organic phase to give luminarine-6 (XIIIa) in the form of a yellow oil with a 53% yield.

TLC: fluorescent silica, system BuOH/AcOH/H₂O 70/20/10: 1 fluorescent spot is developed with ninhydrin, (Rf=0.35).

Mass spectrometry (chemical ionization with ammonia), NERMAG apparatus: the molecular peak +1 is found at 562 in FIG. 1 which represents the spectrum obtained.

EXAMPLE 4

Use of luminarine-6 for marking biotin

Biotin or vitamin H is widely used in biology (immunology, etc) taking advantage of its very high affinity properties ($10^{15} M^{-1}$) for a protein extracted more particularly from egg white, namely avidine, or another extracted from *streptomyces avidinii*, namely streptavidin. Thus, in biological diagnosis methods, it is e.g. possible to mark either avidin, or biotin using a fluorescent or chemiluminescent marker. Here biotin activated by a hydroxysuccinimide group, is reacted with luminarine-6 according to the following reaction:

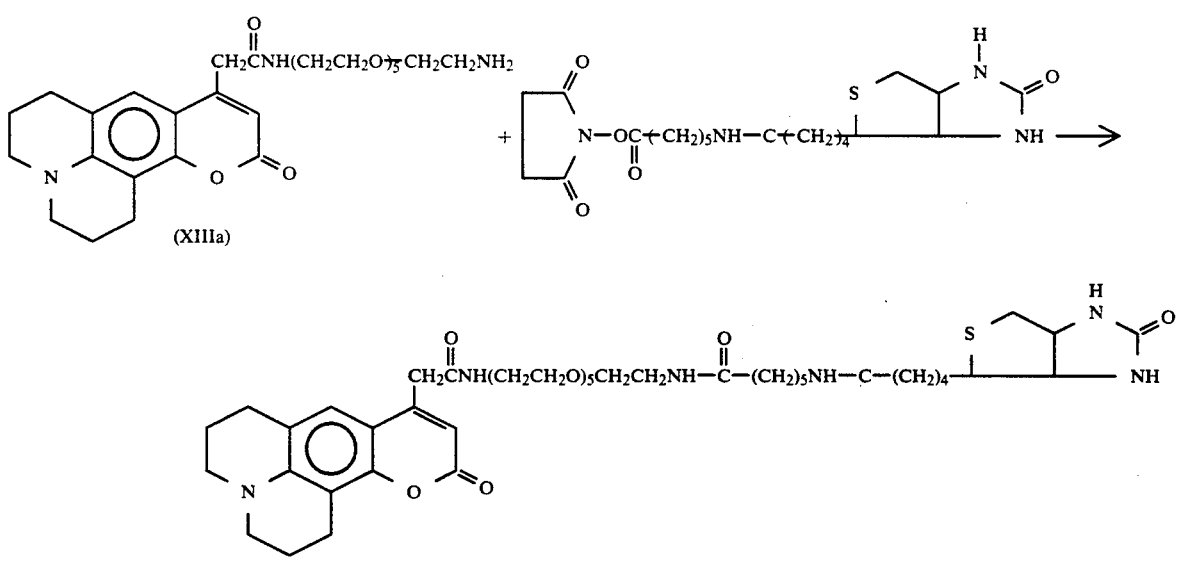

Into a Eppendorf tube containing 1.7 mg of biotin LC.NHS (Pierce) are introduced 1.7 mg of luminarine-6 dissolved in 100 µl of 0.05M bicarbonate solution (pH 8.5). Reaction takes place for 1 hour at 4° C. The effectiveness of the marking is checked by TLC and it is stored at −20° C. in order to react it, without any other treatment, with the avidin at the desired time.

Marking check:

TLC: fluorescent silica, system BuOH/AcOH/H₂O 60/20/20:

The luminarine-6 spot disappears (fluorescent and developed with ninhydrin-Rf=0.35) and a biotin-luminarine spot of Rf=0.5 appears, which is fluorescent and is developed with iodoplatinate (specific reagent of the biotin nucleus).

EXAMPLE 5

Synthesis of luminarine-7 of formula

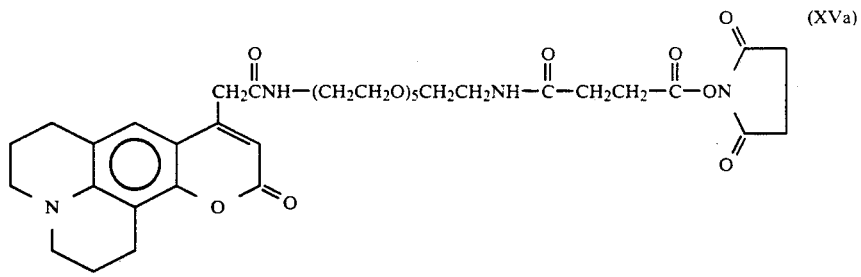

A starting substance is the luminarine-6 described in example 3 and the two following reactions are performed:

a) Action of succinic anhydride on luminarine-6.

The reaction corresponds to the following reaction diagram:

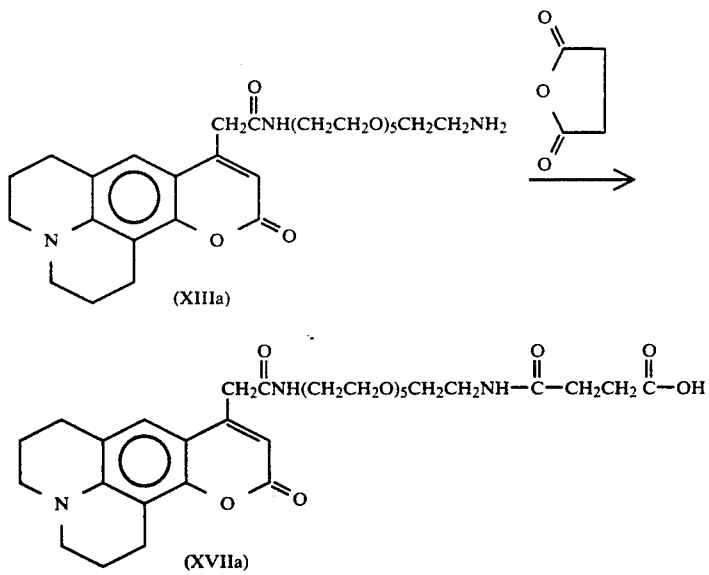

784 mg (1.39 mmole) of liminarine-6 and 140 mg (1.4 mmole) of succinic anhydride dissolved in 10 ml of dichloromethane are stirred for 7 hours at 20° C., protected from light and moisture. Washing takes place with water, followed by drying and evaporation to dryness. This gives a maroon-coloured oil, which will be used as it is for the following stage.

TLC: fluorescent silica, system BuOH/AcOH/H$_2$O 70/20/10.

The luminarine-6 spot disappears and a new fluorescent spot is formed at Rf=0.55.

Mass spectrometry (chemical ionization with ammonia). The molecular peak is found at M=661 in the manner shown in FIG. 2, which shows the spectrum of the derivative (XIVa).

b) Coupling of the acid (XVIIa) with hydroxy succinimide in the presence of dicyclohexyl carbodiimide in accordance with the following diagram:

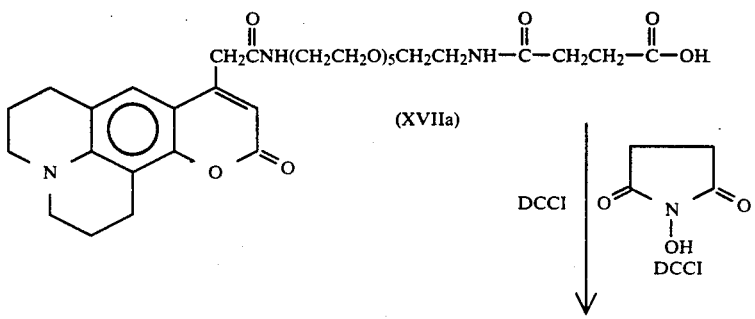

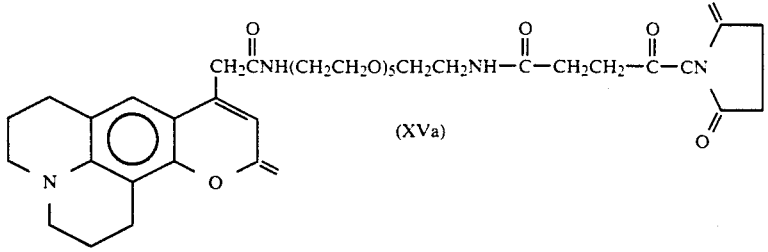

(XVa)

Into a mixture of 250 mg (0.377 mmole) of derivative (XVIIa) in 1 ml of anhydrous dimethyl formamide are introduced 43 mg (0.377 mmole) of hydroxysuccinimide. Cooling takes place to 0° C., followed by the addition of 93 mg of dicyclohexyl carbodiimide (0.45 mmole).

Stirring takes place for 2 hours and then the dicyclohexylurea formed is filtered. The remaining product, luminarine-7, is kept in solution in dimethyl formamide. It can be kept for several months at −20° C. without any deterioration (in the presence of $P_2O_5$). A dried aliquot portion has a total hydrosolubility.

TLC: silica in reverse phase $C_{18}$, system EtOH/-$H_2O$/$NH_4OH$ 70/25/5, fluorescent spot at Rf=0.84.

Reactivity check. The product, in the presence of 3 pentylamine equivalents for 2 hours, reacts and leads to a new fluorescent product of Rf=0.72 (same TLC system).

Mass spectrometry (chemical ionization with ammonia). The largest mass peak found is M=661, as shown in FIG. 3, which shows the spectrum of luminarine-7. This corresponds to the fragmentation mode of hydroxysuccinimide esters.

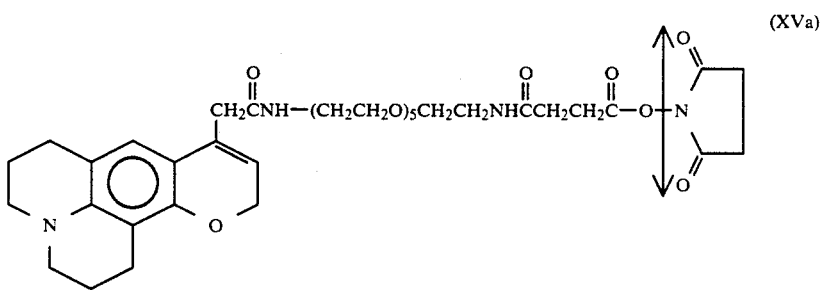

(XVa)

In addition, it is not possible to confuse it with the mass spectrum of the preceding product, because apart from the peak at M=661, the two chromatograms cannot be superimposed.

EXAMPLE 6

Use of luminarine-7 for marking avidin

The amino groups of the protein (avidin) are marked according to the following reaction diagram (avidin/luminarine-7 molar ratio 1:4.7):

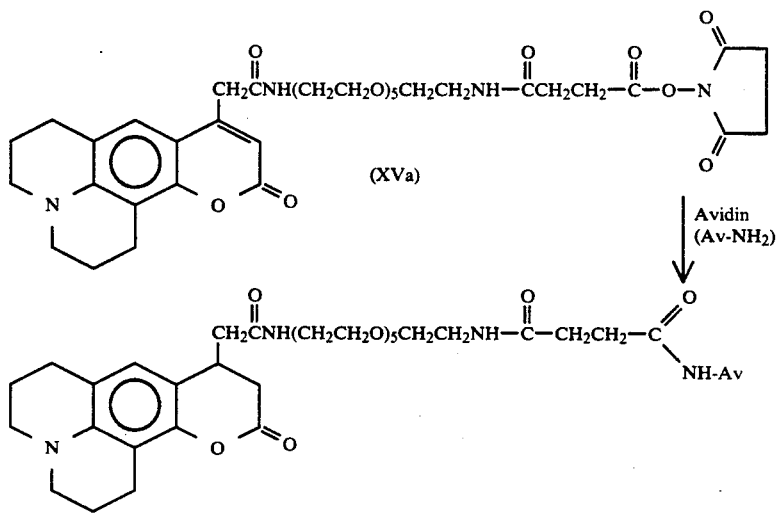

The following stock solutions are prepared: avidin: 10 mg/1 ml, 0.05M bicarbonate buffer; pH 8.5-luminarine 250/mg/1 ml, anhydrous DMF.

1 ml of the avidin solution is introduced into an Eppendorf tube. Addition takes place of 2.12 μl of luminarine solution, accompanied by good stirring. It is left for 1 hour at 4° C. protected from light. The products are then separated on a Pharmacia "fine grade" gel G25 column, equilibrated and eluted with the bicarbonate buffer. The top fraction containing the marked avidin is controlled, subdivided into aliquot portions and kept at −20° C. The check takes place by TLC.

TLC: fluorescent silica, system BuOH/AcOH/H$_2$O 60/20/20.

On the chromatogram the spot of luminarine-7 at Rf 0.48 is no longer observed. There is only a non-migrated spot having the behaviour of avidin and in fluorescent yellow showing that the luminarine is fixed.

EXAMPLE 7

Synthesis of luminarine-8 of formula

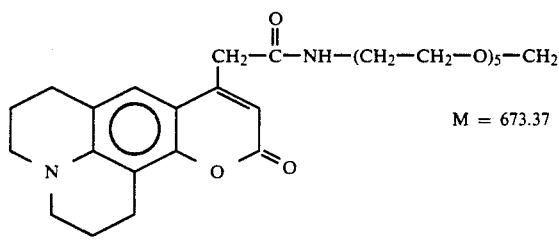

$M = 673.37$

The starting substance is luminarine-7 described in example 5 and the excess hydrazine hydrate is reacted with luminarine-7 according to the following reaction diagram:

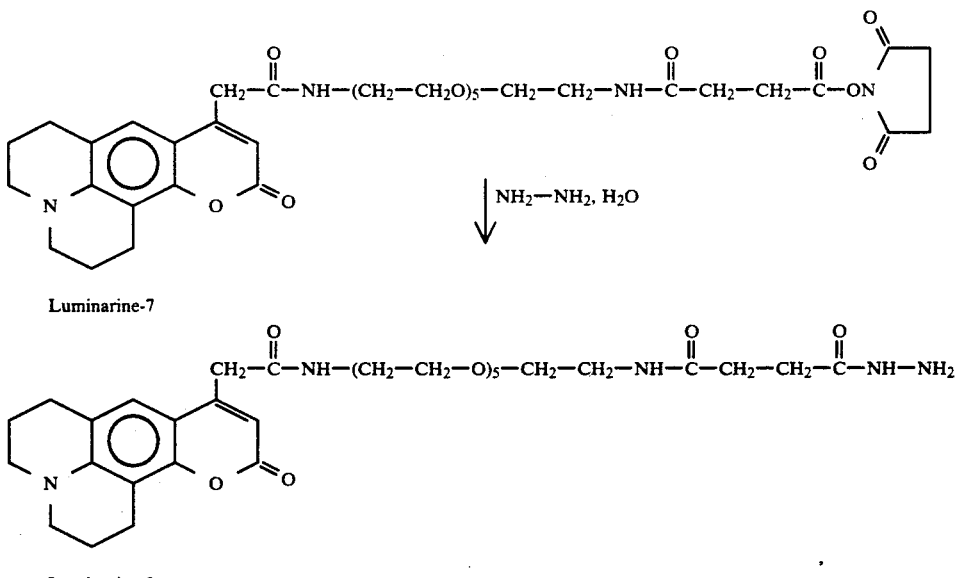

Luminarine-7

Luminarine-8

The starting substance is 630 mg of luminarine-7 (8.3·10$^{-4}$ mmole) in 3 ml of dimethyl formamide (20% solution), followed by dilution with 2 ml of water. 1.5 ml (0.03 mmole) of hydrazine hydrate is introduced and stirring takes place for 3 h. 5 ml of water are added and extraction takes place by 2×15 ml of chloroform. This is followed by drying and evaporation to dryness, which gives 0.3 g of luminarine-8, which corresponds to a 54% yield.

Check:

1) TLC fluorescent silica

System: BuoH/AcoH/H$_2$O 60:20:20

The spot of luminarine-7 (Rf=0.42) and the appearance of a new fluorescent spot of Rf=0.23 are observed.

2) Mass spectrometry (chemical ionization with ammonia).

This spectrum is shown in FIG. 4.

There is indeed a molecular peak at 676+1.

EXAMPLE 8

Synthesis of luminarine-9 of formula

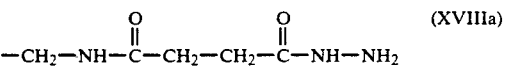

(XIIa)

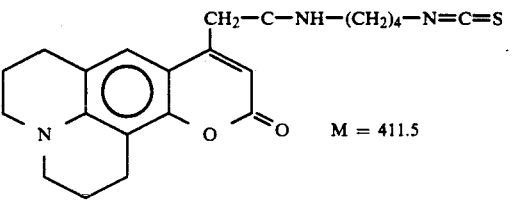

$M = 411.5$

The starting product is luminarine-4 and thiocarbonyl diimidazole is reacted with luminarine-4 according to the following reaction diagram:

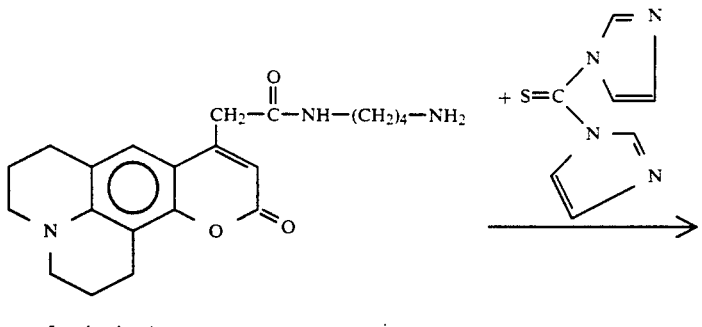

Luminarine-4

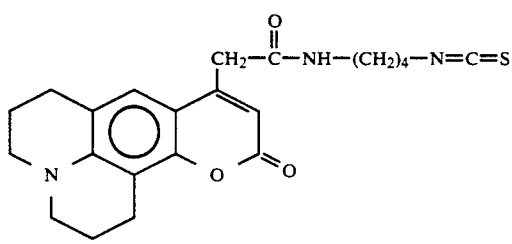

Luminarine-9

535 mg (3 mmole) of thiocarbonyl diimidazole in 15 ml of anhydrous chloroform are dissolved in a 25 ml round-bottomed flask, protected against moisture. Cooling takes place to 5° C. and by fractions 1.1 g (3 mmole) of luminarine-4 are introduced, whilst maintaining the temperature at between 5° and 10° C.

After 2 h at ambient temperature, evaporation to dryness takes place. The residue is purified on a silica gel column as the eluent $CH_2Cl_2$ and then $CH_2Cl_2$-THF 80:20. This is followed by evaporation to dryness and 370 mg of yellow product are obtained with a yield of 30%.

Check:

1) TLC: fluorescent silica system: $CH_2Cl_2$: THF 80:20

The luminarine-4 spot (Rf=0.05) and the appearance of a new fluorescent spot at Rf=0.58 are observed.

2) Mass spectrometry (electron impact)

The spectrum is shown in FIG. 5. The molecular peak is at 411.

EXAMPLE 9

Reaction of luminarine-9 with pentyl amine

Pentyl amine is marked with luminarine-9 according to the following reaction diagram:

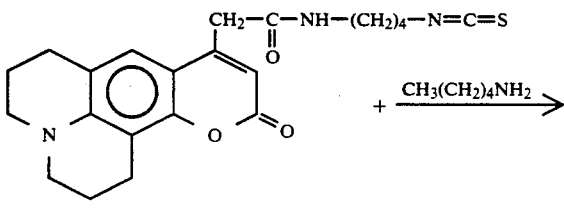

Luminarine-9

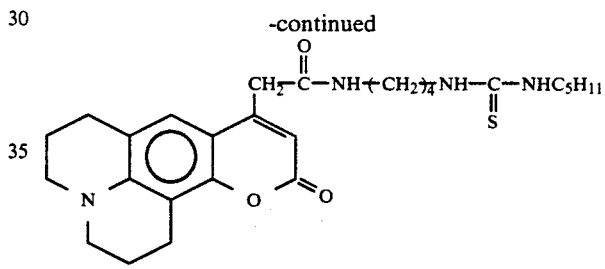

In a 4 ml "reacti-vial" are dissolved 130 mg (0.315 mmol) of luminarine-9 in 2.6 ml of dichloromethane, followed by the introduction of 109 μl (82 mg)-0.94 mmol) of pentyl amine.

Stirring takes place for 2 h at ambient temperature (the TLC check indicating a quantitative reaction). Crystallization takes placed at 5° C. for 48 h, followed by filtration and drying with a yield of 77%, i.e. 120 mg.

Check:

1) TLC fluorescent silica

System: $CH_2Cl_2$: THF 80:20

A single fluorescent spot at Rf=0.32 is observed, whereas the luminarine-9 has a spot at Rf=0.58.

2) Mass spectrometry

This spectrum is shown in FIG. 6. It is possible to see a small molecular peak at 498, as well as a large fragment at 411. The spectrum is completely different from that of luminarine-9.

EXAMPLE 10

In order to reveal the improved properties of the luminarines according to the invention, fluorescence, absorbance and chemiluminescence measurements were carried out using as the fluorogen prior art coumarins, namely coumarine-1 ®, dimethylamino-7 methyl-4 coumarin (DEMC) of formula:

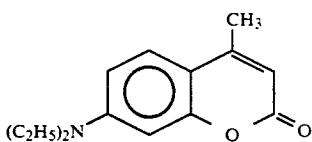

and coumarine-311 ®, dimethylamino-7 methyl-4 coumarin (DMMC) of formula:

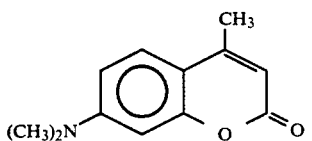

in order to compare them with coumarine-102 ®, tetrahydro-2,3,5,6,7,1H,5H,11H-(1)-benzopyrano(6,7,8-ij)methyl-9 quinolizinone-11 (TBMQ), which is the basic nucleus of the derivatives according to the invention of formula:

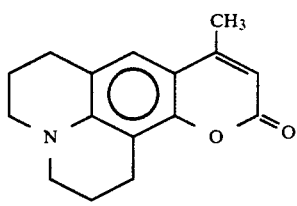

The fluorescence measurements are carried out with a Perkin Elmer LS5 spectrifluorometer with 2 nm slit widths for two monochromators.

The absorbance measurements were carried out with a Jobin Yvon JY3 spectrophotometer. The chemiluminescence measurements were obtained by using a Jobin Yvon JY4 spectrofluorimeter with 10 nm slit widths. The cell for the liquid samples is a 10×10 mm quart cell with a capacity of 3 ml and filled with 2 ml of solution, which corresponds to a real solution volume exposed to the photomultiplier of 1.35 ml.

Fluorescence and Absorbance Measurements

These measurements were carried out at 20+2° C. and the quantum efficiencies of fluorescence $R_F$ of coumarins-1, 311 and 102 were determined compared with quinine disulphate, whose fluorescence quantum efficiency is 0.546 using the Parker method described in Analyst, 85, 1960, p. 587 using a 2 mg/l quinine disulphate solution in 0.1N $H_2SO_4$.

For the coumarins, use was made of a solution of acetone and ethyl acetate in a volume ratio of 75:25 with a $10^{-6}$ mole/l coumarin concentration ensuring in each case an absorbance below 0.05.

Chemiluminescence Measurements

In order to determine the chemiluminescence quantum efficiencies $R_c$, the intensity was estimated as a function of time at the emission maximum. When the intensity decrease is relatively low, the emission spectrum is plotted and then the intensity is followed as a function of time until it has dropped to 2% of the maximum intensity.

The other luminescence parameters are measured directly. These consist of the maximum intensity (lmax), the time for reaching the maximum intensity (Tmax) and the time for reaching half the maximum intensity following the maximum time (T½).

The chemi luminescence efficiency $R_c$ is calculated by the Rauhut method described in J. Am. Chem. Soc., 88, 15, 1966, p.3604.

The excitation efficiency $R_{ex}$ is determined on the basis of the formula:

$$R_C = R_{ex} \times R_F .$$

For chemiluminescence measurements with TCPO, to 1 ml of the solution containing $10^{-3}$ mole/l of coumarin are added 0.5 ml of a $2 \cdot 10^{-3}$ mole/l TCPO solution in ethyl acetate, 0.5 ml of a $2 \cdot 10^{-2}$ mole/l $H_2O_2$ solution in acetone and 10 μl of a 0.1 mole/l imidazole nitrate buffer at pH 7.5. When DNPO is used, to the same solution of coumarin in acetone are added 0.5 ml of a $10^{-3}$ mole/l DNPO solution in ethyl acetate and 0.5 ml of a $10^{-2}$ mole/l $H_2O_2$ solution in acetone.

The fluorescence and absorbance properties of coumarins are given in table 1 and the chemiluminescence results are given in table 2.

On the basis of tables 1 and 2, it can be seen that the coumarin nucleus used in the invention and which corresponds to coumarin 102 has better fluorescence, absorbance and chemiluminescece properties.

Table 3 gives the results obtained with respect to the chemiluminescence efficiency $R_C$ using TCPO and $H_2O_2$ as a function of the coumarin-102 concentration, together with the values for Tmax, lmax and T½.

These results make it clear that the chemiluminescence efficiency increases with the coumarin-102 concentration.

Table 4 gives the variations of the chemiluminescence efficiency, lmax, Tmax and T½, as a function of the pH of the solution. The results obtained demonstrate that the chemiluminescence efficiency increases up to pH6 and then decreases. However, the values for Tmax and T½ decrease when the pH increases beyond 5. The maximum intensity increases significantly with the pH.

TABLE 1

|  | $RF^1$ | ε 365 nm | S $10^3$ |
|---|---|---|---|
| COUMARINE-102 | 0.57 | 23 100 | 36 |
| COUMARINE-1 | 0.55 | 38 000 | 57 |
| COUMARINE-311 | 0.52 | 26 900 | 40 |

$R_F$ = fluorescence quantum efficiency
ε = molecular extinction coefficient
S = fluorescence sensitivity

TABLE 2

|  | DMPO | | TCPO | |
|---|---|---|---|---|
|  | $R_C$ $10^2 E \cdot mole^{-1}$ | $R_E$ $10^2$ | $R_C$ $10^2 E \cdot mole^{-1}$ | $R_E$ $10^2$ |
| COUMARINE-102 | 0.26 | 0.45 | 0.37 | 0.65 |
| COUMARINE-1 | 0.18 | 0.33 | 0.37 | 0.67 |
| COUMARINE-311 | 0.13 | 0.24 | 0.17 | 0.32 |

$R_C$ = chemiluminescence quantum efficiency
$R_E$ = excitation efficiency
DMPO = bis-(dinitro-2,4 phenyl)oxalate
TCPO = bis-(trichloro-2,4,6 phenyl) oxalate.

TABLE 3

| $(C_{102})$ $E \cdot mole^{-1}$ | $R_C \times 10^4$ $E \cdot mole^{-1}$ | Imax A.U. | Tmax min. | T½ min. |
|---|---|---|---|---|
| $1.4 \times 10^{-5}$ | 12.0 | 301 | 0.2 | 0.10 |
| $1.4 \times 10^{-6}$ | 4.14 | 75 | 0.2 | 0.15 |
| $1.4 \times 10^{-7}$ | 2.31 | 31 | 0.2 | 0.12 |
| $1.4 \times 10^{-8}$ | 0.40 | 3.2 | 0.2 | 0.10 |
| $1.4 \times 10^{-9}$ | 0.20 | 0.3 | 0.2 | 0.08 |

TABLE 4

| pH | $R_C \times 10^4$ $E \cdot mole^{-1}$ | Imax A.U. | Tmax min. | T½ min. |
|---|---|---|---|---|
| 4 | 1.52 | 24 | 0.8 | 5.0 |
| 5 | 1.58 | 17 | 1.0 | 6.0 |
| 6 | 2.34 | 25 | 0.8 | 5.6 |
| 7 | 2.23 | 110 | 0.4 | 1.8 |
| 8 | 1.60 | 245 | 0.2 | 0.4 |

We claim:
1. Compound in accordance with the formula:

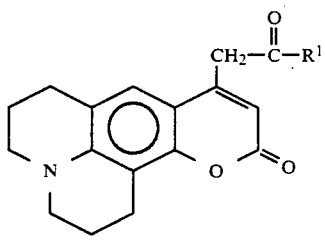 (I)

in which $R^1$ represents:
1) —NH—$(CH_2)_n$—$R^2$ with n being an integer from 1 to 20 and $R^2$ representing —N=C=S or NH—CO—$CH_2$X with X representing I, Br or Cl, or
2) —NH—$(CH_2—CH_2—O)_m$—$CH_2$—$CH_2$—$R^3$ with m being an integer from 1 to 30 and $R^3$ representing a group chosen from among those of formula

—$NH_2$

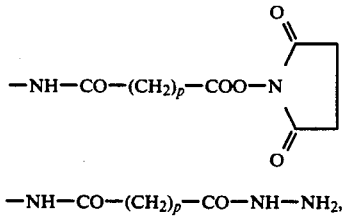

—NH—CO—$(CH_2)_p$—CO—NH—$NH_2$,

—N=C=S, and

—NH—CO—$CH_2$X in which p is an integer from 1 to 10 and X represents I, Br or Cl.

2. Compound in accordance with the formula:

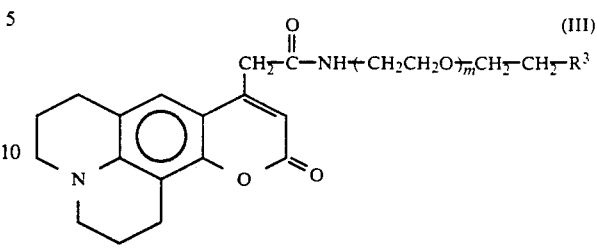 (III)

in which n is an integer from 1 to 20 and $R^2$ represents —N=C=S or NH—CO—$CH_2$X with X representing I, Br or Cl.

3. Compound according to claim 2, wherein n is equal to 4.

4. Compound in accordance with the formula:

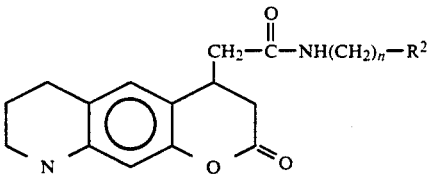

in which m is an integer from 1 to 30 and $R^3$ is as defined in claim 1.

5. Compound according to claim 4, wherein m is equal to 5.

6. Compound according to claim 5, wherein $R^3$ is $NH_2$.

7. Compound according to claim 5, wherein $R^3$ is

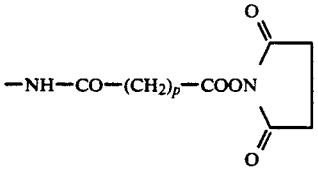

with p being an integer from 1 to 10.

8. Compound according to claim 7, wherein p is equal to 2.

9. Compound according to claim 5, wherein $R^3$ is

—NH—CO$(CH_2)_p$CONH—$NH_2$.

10. Compound according to claim 9, wherein p is equal to 2.

* * * * *

UNITED STATES PATENT AND TRADEMARK OFFICE
CERTIFICATE OF CORRECTION

PATENT NO. : 5,151,517

DATED : September 29, 1992

INVENTOR(S) : Pierre Reveilleau et al.

It is certified that error appears in the above-identified patent and that said Letters Patent is hereby corrected as shown below:

Delete "coumar in" and insert --coumarin-- at each of the following occurrences: Column 1, line 67, Column 8, lines 35 and 68, Column 10, line 67, Column 12, line 2, Column 13, lines 3, 39 and 60, Column 30, line 34;

Column 18, line 32, delete "($1 \cdot 10--2$mmole) and insert --($1 \cdot 10^{-2}$mmole)--.

Column 28, lines 42 and 44, delete "mmol)" and insert --mmole)--.

Column 30, line 3, delete "chemi luminescence" and insert --chemiluminescence--.

Column 30, line 66, delete "DMPO" and insert --DNPO--.

UNITED STATES PATENT AND TRADEMARK OFFICE
CERTIFICATE OF CORRECTION

PATENT NO. : 5,151,517

DATED : September 29, 1992

INVENTOR(S) : Pierre Reveilleau et al.

It is certified that error appears in the above-identified patent and that said Letters Patent is hereby corrected as shown below:

Delete claim 4 and substitute the following:

4. Compound in accordance with the formula:

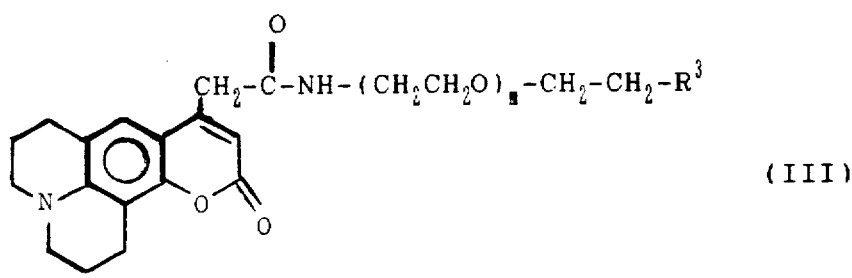

(III)

in which m is an integer from 1 to 30 and $R^3$ is as defined in claim 1.

Signed and Sealed this

Eighth Day of February, 1994

BRUCE LEHMAN

*Attest:*

*Attesting Officer*   *Commissioner of Patents and Trademarks*

UNITED STATES PATENT AND TRADEMARK OFFICE
CERTIFICATE OF CORRECTION

PATENT NO. : 5,151,517

DATED : September 29, 1992

INVENTOR(S) : Pierre Reveilleau et al.

It is certified that error appears in the above-identified patent and that said Letters Patent is hereby corrected as shown below:

Delete claim 2 and substitute the following:

2. Compound in accordance with the formula:

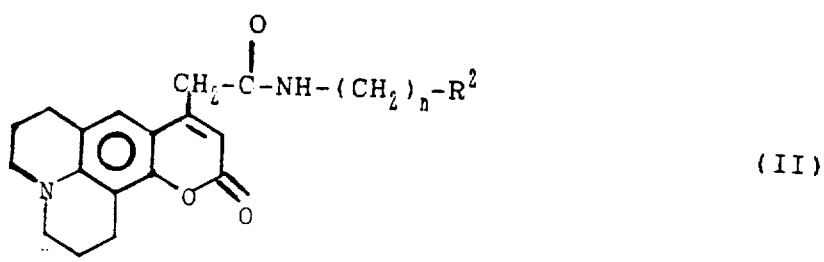

(II)

in which n in an integer from 1 to 20 and $R^2$ represents $-N=C=S$ or $NH-CO-CH_2X$ with X representing I, Br or Cl.

Signed and Sealed this

Twenty-first Day of June, 1994

Attest:

BRUCE LEHMAN

Attesting Officer       Commissioner of Patents and Trademarks